United States Patent [19]
Rane et al.

[11] Patent Number: 5,958,940
[45] Date of Patent: Sep. 28, 1999

[54] TRICYCLIC COMPOUNDS USEFUL AS INHIBITORS OF FARNESYL-PROTEIN TRANSFERASE

[75] Inventors: Dinanath F. Rane, Morganville; Alan B. Cooper, West Caldwell; Alan K. Mallams, Hackettstown; Ronald J. Doll, Maplewood; F. George Njoroge, Union; Arthur G. Taveras, Rockaway, all of N.J.

[73] Assignee: Schering Corporation, Kenilworth, N.J.

[21] Appl. No.: 08/927,728

[22] Filed: Sep. 11, 1997

Related U.S. Application Data

[60] Provisional application No. 60/028,925, Sep. 13, 1996.
[51] Int. Cl.⁶ .......................... A61K 31/44; C07D 401/14
[52] U.S. Cl. .............................. 514/290; 546/93
[58] Field of Search ................. 546/93; 514/290

[56] References Cited

U.S. PATENT DOCUMENTS 5,696,121 12/1997 Bishop ........................... 514/254
5,703,090 12/1997 Afonso ........................... 514/290

FOREIGN PATENT DOCUMENTS

| | | |
|---|---|---|
| 0 396 083 | 11/1990 | European Pat. Off. . |
| 1 593 417 | 7/1981 | United Kingdom . |
| WO 92 00293 | 1/1992 | WIPO . |
| WO 95 10515 | 4/1995 | WIPO . |
| WO 95 10516 | 4/1995 | WIPO . |
| WO 97 18813 | 5/1997 | WIPO . |

OTHER PUBLICATIONS

Khosravi–Far R et al. Cell Growth & Differentiation. 3, pp. 461–469, Jul. 1992.

*Primary Examiner*—Evelyn Mei Huang
*Attorney, Agent, or Firm*—Joseph T. Majka

[57] ABSTRACT

Novel tricyclic compounds and pharmaceutical compositions are disclosed which are inhibitors of the enzyme, farnesyl protein transferase. Also disclosed is a method of inhibiting Ras function and therefore inhibiting the abnormal growth of cells. The method comprises administering the novel tricyclic compound to a biological system. In particular, the method inhibits the abnormal growth of cells in a mammals such as a human.

17 Claims, No Drawings

TRICYCLIC COMPOUNDS USEFUL AS INHIBITORS OF FARNESYL-PROTEIN TRANSFERASE

This application claims the benefit of provisional application 60/028,925 filed Sep. 13, 1996.

BACKGROUND

Patent application WO 95/00497 published Jan. 5, 1995 under the Patent Cooperation Treaty (PCT) describes compounds which inhibit the enzyme, farnesyl-protein transferase (FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras. Several compounds of this invention have been demonstrated to have anti-tumor activity in animal models.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds useful in the claimed methods are represented by Formula 1.0:

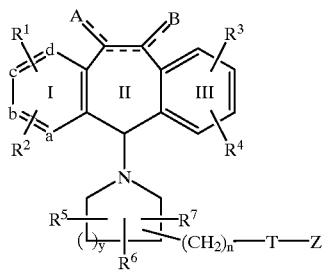

(1.0)

or a pharmaceutically acceptable salt or solvate thereof, wherein:

one of a, b, c and d represents N or $NR^9$ wherein $R^9$ is O—, —$CH_3$ or —$(CH_2)_nCO_2H$ wherein n is 1 to 3, and the remaining a, b, c and d groups represent $CR^1$ or $CR^2$; or each of a, b, c, and d are independently selected from $CR^1$ or $CR^2$; each $R^1$ and each $R^2$ is independently selected from H, halo, —$CF_3$, —$OR^{10}$ (e.g., —$OCH_3$), —$COR^{10}$, —$SR^{10}$ (e.g., —$SCH_3$ and —$SCH_2C_6H_5$), —$S(O)_tR^{11}$ (wherein t is 0, 1 or 2, e.g., —$SOCH_3$ and —$SO_2CH_3$), —SCN, —$N(R^{10})_2$, —$NR^{10}R^{11}$, —$NO_2$, —$OC(O)R^{10}$, —$CO_2R^{10}$, —$OCO_2R^{11}$, —CN, —NHC(O)$R^{10}$, —$NHSO_2R^{10}$, —$CONHR^{10}$, —$CONHCH_2CH_2OH$, —$NR^{10}COOR^{11}$, —$SR^{11}C(O)OR^{11}$ (e.g., —$SCH_2CO_2CH_3$), —$SR^{11}N(R^{75})_2$ wherein each $R^{75}$ is independently selected from H and —C(O)$OR^{11}$ (e.g., —$S(CH_2)_2NHC(O)$O-t-butyl and —$S(CH_2)_2NH_2$), benzotriazol-1-yloxy, tetrazol-5-ylthio, or substituted tetrazol-5-ylthio (e.g., alkyl substituted tetrazol5-ylthio such as 1-methyl-tetrazol-5-ylthio), alkynyl, alkenyl or alkyl, said alkyl or alkenyl group optionally being substituted with halo, —$OR^{10}$ or —$CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$ and $R^6$ (y=0) or $R^5$, $R^6$ and $R^7$ (y=1) each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or one of $R^5$, $R^6$ and $R^7$ can be taken in combination with $R^{40}$ as defined below to represent —$(CH_2)_r$— wherein r is 1 to 4 which can be substituted with lower alkyl, lower alkoxy, —$CF_3$ or aryl, or $R^5$ is combined with $R^6$ or $R^7$ to represent =O or =S;

$R^{10}$ independently represents H, alkyl, cycloalkyl, cycloalkylalkyl, heteroaryl, aryl, aralkyl or —$NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl, cycloalkylalkyl, alkenyl and alkynyl;

$R^{11}$ represents alkyl or aryl;

the dotted line between carbon atoms 5 and 6 represents an optional double bond, such that when a double bond is present, A and B independently represent —$NO_2$, —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$, H and halo, dihalo, alkyl and H, (alkyl)$_2$, —H and —$OC(O)R^{10}$, H and —$OR^{10}$, oxy, aryl and H, =$NOR^{10}$ or —O—$(CH_2)_p$—O— wherein p is 2, 3 or 4; and y is 0 (zero) or 1;
n is 0, 1, 2, 3, 4, 5 or 6;
T is —CO—; —SO—; —$SO_2$—; or —$CR^{30}R^{31}$— wherein $R^{30}$ and $R^{31}$ independently represent H, alkyl, aryl, aralkyl, heteroalkyl, heteroaryl, heteroarylalkyl, heterocycloalkyl or heterocycloalkylalkyl;
Z represents alkyl, aryl, aralkyl, heteroalkyl, heteroaryl, heteroarylalkyl, heterocycloalkyl, heterocycloalkylalkyl, —$OR^{40}$, —$SR^{40}$, —$CR^{40}R^{42}$ or —$NR^{40}R^{42}$ wherein $R^{40}$ and $R^{42}$ are defined hereinbefore

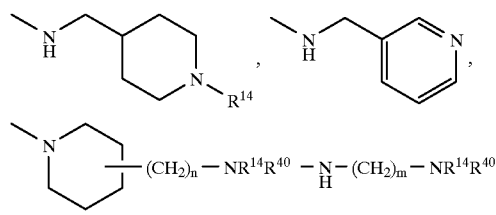

wherein n, $R^{40}$ and $R^{42}$ are defined hereinbefore,
m is 2, 3 4, 5, 6, 7 or 8;
and $R^{14}$ represents H, $C_{1-6}$ alkyl, aralkyl, acyl, carboxamido, cyano, alkoxycarbonyl, aralkyloxycarbonyl, D- and L-amino acids covalently bonded through the carboxyl group, imido, imidamido, sulfamoyl, sulfonyl, dialkylphosphinyl, N-glycosyl,

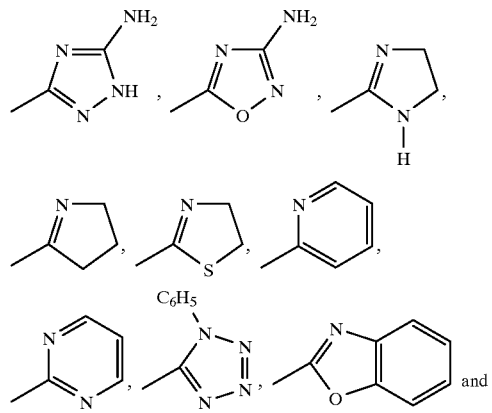

—$C(NHCH_3)$=$CHNO_2$,
with the proviso that when T is —SO—, Z is not —$NR^{40}R^{42}$.

In the compounds of Formula (1.0), preferably a is N and b, c and d are carbon. Preferably A and B each represent $H_2$ and the optional double bond is absent. Also preferred is that $R^1$ and $R^4$ are H, and $R^2$ and $R^3$ are halo, preferably independently Br or Cl. For example, $R^2$ is Br and $R^3$ is Cl. These compounds include compounds wherein $R^2$ is in the 3-position and $R^3$ is in the 8-position, e.g., 3-Br and 8-Cl.

Also, compounds of Formula (1.0) preferably include compounds wherein $R^1$ is H, and $R^2$, $R^3$ and $R^4$ are halo, preferably independently selected from Br or Cl. These compounds include compounds wherein $R^2$ is in the 3-position, $R^3$ is in the 7-position and $R^4$ is in the 8-position, e.g., 3-Br, 7-Br, 8-Cl. Also included are compounds wherein $R^2$ is in the 3-position, $R^3$ is in the 8-position and $R^4$ is in the 10-position, e.g. 3-Br, 8-Cl and 10-Br.

Preferably n is zero. Also preferred is that the moiety —$(CH_2)_n$—T—Z is bonded at the 2-position on the pyrrolidine or azetidine ring. Also preferred is that T is —CO— and Z is —$NR^{40}R^{42}$, more preferably where one of $R^{40}$ or $R^{42}$ is H. Also preferred is that $R^{40}$ is H and $R^{42}$ is 3-pyridylmethyl.

In another embodiment, the present invention is directed toward a pharmaceutical composition for inhibiting the abnormal growth of cells comprising an effective amount of compound (1.0) in combination with a pharmaceutically acceptable carrier.

In another embodiment, the present invention is directed toward a method for inhibiting the abnormal growth of cells, including transformed cells, comprising administering an effective amount of compound (1.0) to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells. Also, the inhibition of the abnormal growth of cells by the treatment with compound (1.0) may be by inhibiting ras farnesyl protein transferase. The inhibition may be of tumor cells wherein the Ras protein is activated as a result of oncogenic mutation in genes other than the Ras gene. Alternatively, compounds (1.0) may inhibit tumor cells activated by a protein other than the Ras protein.

This invention also provides a method for inhibiting tumor growth by administering an effective amount of compound (1.0) to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the carbonyl piperazinyl and piperidinyl compounds (1.0) described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, Src, abl, lck, and fyn), may be inhibited by the carbonyl piperazinyl and piperidinyl compounds (1.0) described herein.

In another embodiment, the present invention is directed toward a method for inhibiting ras farnesyl protein transferase and the farnesylation of the oncogene protein Ras by administering an effective amount of compound (1.0) to mammals, especially humans. The administration of the compounds of this invention to patients, to inhibit farnesyl protein transferase, is useful in the treatment of the cancers described above.

DETAILED DESCRIPTION OF THE INVENTION

The following solvents and reagents are referred to herein by the abbreviations indicated:

tetrahydrofuran (THF);
ethanol (EtOH);
methanol (MeOH);
ethyl acetate (EtOAc);
N,N-dimethylformamide (DMF);
trifluoroacetic acid (TFA);
1-hydroxybenzotriazole (HOBT);
1-(3-dimethylaminopropyl)-3-ethyl carbodiimide hydrochloride (DEC);
dimethylsulfoxide (DMSO);
acetic acid (HOAC or ACOH)
4-methylmopholine (NMM);
dimethylaminopyridine (DMAP); and
dimethoxyethane (DME).
t-butoxycarbonyl (BOC)
acetyl(OAc)

As used herein, the following terms are used as defined below unless otherwise indicated:

◀ or ⦀⦀⦀—indicates a pure isomer;

――—when attached to a carbon atom labeled with an asterisk (*), indicates a separated isomer whose stereochemistry is not established;

⁓—indicates a racemic mixture;

M⁺—represents the molecular ion of the molecule in the mass spectrum;

MH⁺—represents the molecular ion plus hydrogen of the molecule in the mass spectrum;

PMR or NMR refers to proton magnetic resonance spectroscopy or nuclear magnetic resonance spectroscopy, whose terms are interchangeable;

Bu-represents butyl;
Et-represents ethyl;
Me-represents methyl;
Ph-represents phenyl;

benzotriazol-1-yloxy represents

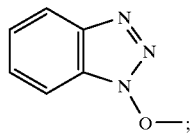

1-methyl-tetrazol-5-ylthio represents

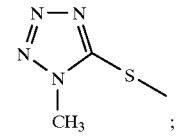

acyl-a moiety of the formula —COR$^{15}$ wherein R$^{15}$ represents H, C$_{1-6}$ alkyl, aryl, aralkyl, heteroalkyl, heteroaryl, heteroarylalkyl, heterocycloalkyl and heterocycloalkylalkyl;

alkyl-(including the alkyl portions of alkoxy, alkylamino and dialkylamino)-represents straight and branched carbon chains and contains from one to twenty carbon atoms, preferably one to six carbon atoms (i.e. C$_{1-6}$ alkyl); for example methyl, ethyl, propyl, iso-propyl, n-butyl, t-butyl, n-pentyl, isopentyl, hexyl and the like; wherein said alkyl and said C$_{1-6}$ alkyl group may be optionally and independently substituted with one, two, three or more of the following: halo, alkyl, aryl, alkoxy, amino (—NH$_2$), alkylamino, cyano (—CN), —CF$_3$, dialkylamino, hydroxy, oxy (=O), phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —NCOR$^{10}$ or —COOR$^{10}$.

alkoxy—an alkyl moiety of one to 20 carbon atoms covalently bonded to an adjacent structural element through an oxygen atom, for example, methoxy, ethoxy, propoxy, butoxy, pentoxy, hexoxy and the like; wherein said alkoxy group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —CONR$^{10}$, —NCOR$^{10}$ or —COOR$^{10}$;

alkoxycarbonyl—represents a alkoxy moiety, as defined above, covalantly bonded to a carbonyl moiety (—CO—) through an oxygen atom, for example, —COOCH$_3$, —COOCH$_2$CH$_3$ and —COOC(CH$_3$)$_3$;

alkenyl—represents straight and branched carbon chains having at least one carbon to carbon double bond and containing from 2 to 12 carbon atoms, preferably from 2 to 6 carbon atoms and most preferably from 3 to 6 carbon atoms; wherein said alkenyl group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —CONR$^{10}$, —NCOR$^{10}$ or —COOR$^{10}$;

alkynyl-represents straight and branched carbon chains having at least one carbon to carbon triple bond and containing from 2 to 12 carbon atoms, preferably from 2 to 6 carbon atoms; wherein said alkynyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

amino acid- refers to organic compounds having both an amino group (—$NH_2$) and a carboxyl group (—COOH). Representative amino acids include glycine, serine, alanine, phenylalanine, tyrosine, S-methyl methionine and histidine;

aryl (including the aryl portion of aralkyl)—represents a carbocyclic group containing from 6 to 15 carbon atoms and having at least one aromatic ring (e.g., aryl is phenyl), wherein said aryl group optionally can be fused with aryl, cycloalkyl, heteroaryl or heterocycloalkyl rings; and wherein any of the available substitutable carbon and nitrogen atoms in said aryl group and/or said fused ring(s) may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

aralkyl—represents an alkyl group, as defined above, wherein one or more hydrogen atoms of the alkyl moiety have been substituted with one or more aryl groups; wherein said aralkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$; Representative aralkyl groups include benzyl and diphenylmethyl;

aralkyloxy—represents an aralkyl group, as defined above, covalently bonded to an adjacent structural element through an oxygen atom, for example, phenylmethyloxy and phenylethyloxy;

aralkyloxycarbonyl—represents an aralkyloxy group, as defined above, covalantly bonded to a carbonyl moiety (—CO—) through an oxygen atom, for example, —$COOCH_2C_6H_5$ and —$COOCH_2CH_2C_6H_5$;

carboxamido—represents a moiety of the formula —$CONH_2$ or —$CONR^{40}R^{42}$;

cycloalkyl—represents saturated carbocyclic rings branched or unbranched of from 3 to 20 carbon atoms, preferably 3 to 7 carbon atoms; wherein said cycloalkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^1$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

cycloalkylalkyl—represents an alkyl group, as defined above, wherein one or more hydrogen atoms of the alkyl moiety have been substituted with one or more cycloalkyl groups; wherein said cycloalkylalkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

halo—represents fluoro, chloro, bromo and iodo;

heteroalkyl—represents straight and branched carbon chains containing from one to twenty carbon atoms, preferably one to six carbon atoms interrupted by 1 to 3 heteroatoms selected from —O—, —S— and —N—; wherein any of the available substitutable carbon and nitrogen atoms in said heteroalkyl chain may be optionally and independendently substituted with one, two, three or more of the following: halo, $C_1$-$C_6$ alkyl, aryl, cyano, hydroxy, alkoxy, oxy, phenoxy, —$CF_3$, —$OCF_3$, amino, alkylamino, dialkylamino, heterocycloalkyl, —$SO_2NH_2$, —$NHSO_2R^{10}$, —$SO_2NHR^{10}$, —$SO_2R^{10}$, —$SOR^{10}$, —$SR^{10}$ or —$NHSO_2$, —$NO_2$, —$CONR^{10}$, —$NCOR^{10}$ or —$COOR^{10}$;

heteroaryl—represents cyclic groups having at least one heteroatom selected from O, S and N, said heteroatom(s) interrupting a carbocyclic ring structure and having a sufficient number of delocalized pi electrons to provide aromatic character, with the aromatic heterocyclic groups containing from 2 to 14 carbon atoms,wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independendently substituted with one, two, three or more of the following: halo, $C_1$-$C_6$ alkyl, aryl, cyano, hydroxy, alkoxy, oxy, phenoxy, —$CF_3$, —$OCF_3$, amino, alkylamino, dialkylamino, heterocycloalkyl, —$SO_2NH_2$, —$NHSO_2R^{10}$, —$SO_2NHR^{10}$, —$SO_2R^{10}$, —$SOR^{10}$, —$SR^{10}$, or —$NHSO_2$, —$NO_2$, —$CONR^{10}$, —$NCOR^{10}$ or —$COOR^{10}$. Representative heteroaryl groups can include, for example, furanyl, imidazoyl, pyrimidinyl, triazolyl, 2-, 3- or 4-pyridyl or 2-, 3- or 4-pyridyl N-oxide wherein pyridyl N-oxide can be represented as:

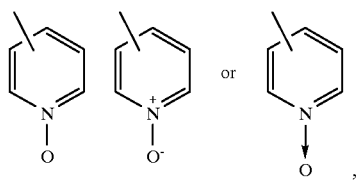

heteroarylalkyl—represents an alkyl group, as defined above, wherein one or more hydrogen atoms have been replaced by one or more heteroaryl groups; wherein said heteroarylalkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —SO₂NH₂, —NHSO₂R¹⁰, —SO₂NHR¹⁰, —SO₂R¹⁰, —SOR¹⁰, —SR¹⁰, —NHSO₂, —NO₂, —CONR¹⁰, —NCOR¹⁰ or —COOR¹⁰; as exemplified by 2-, 3- or 4-pyridylmethyl or 2-, 3- or 4-pyridylmethyl N-oxide;

heterocycloalkyl-represents a saturated, branched or unbranched carbocylic ring containing from 3 to 15 carbon atoms, preferably from 4 to 6 carbon atoms, which carbocyclic ring is interrupted by 1 to 3 heteroatoms selected from —O—, —S— and —N—, wherein optionally, said ring may contain one or two unsaturated bonds which do not impart aromatic character to the ring; and wherein any of the available substitutable carbon and nitrogen atoms in the ring may be optionally and independently substituted with one, two, three or more of the following: halo, alkyl, aryl, alkoxy, amino, alkylamino, cyano, —CF₃, dialkylamino, hydroxy, oxy, phenoxy, —OCF₃, heterocycloalkyl, —SO₂NH₂, —NHSO₂R¹⁰, —SO₂NHR¹⁰, —SO₂R¹⁰, —SOR¹⁰, —SR¹⁰, —NHSO₂, —NO₂, —CONR¹⁰, —NCOR¹⁰ or -COOR¹⁰

Representative heterocycloalkyl groups can include 2- or 3-tetrahydrofuranyl, 2- or 3-tetrahydrothienyl, 1-, 2-, 3- or 4-piperidinyl, 2- or

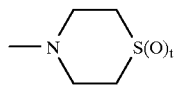

3-pyrrolidinyl, 1-, 2- or 3-piperizinyl, 2- or 4-dioxanyl, wherein t is 0, 1 or 2; morpholinyl,heterocycloalkylalkyl-represents an alkyl group, as defined above, wherein one or more hydrogen atoms have been replaced by one or more heterocycloalkyl groups; wherein optionally, said ring may contain one or two unsaturated bonds which do not impart aromatic character to the ring; and wherein said heterocycloalkylalkyl group may be optionally and independently substituted with one, two, three or more of the following: halo, alkyl, aryl, alkoxy, amino, alkylamino, cyano, —CF₃, dialkylamino, hyciroxy, oxy, phenoxy, —OCF₃, heterocycloalkyl, —SO₂NH₂, —NHSO₂R¹⁰, —SO₂NHR¹⁰, —SO₂R¹⁰, —SOR¹⁰, —SR¹⁰, —NHSO₂, —NO₂, —CONR¹⁰, —NCOR¹⁰ or —COOR¹⁰;

imido—represents a moiety of the formula

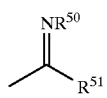

wherein and R⁵⁰ represents H, cyano, aryl, —SO₂NH₂, —SO₂NR⁴⁰R⁴² and carboxamido and R⁵¹ represents aryl and aryloxy. Representative imido groups can include, for example,

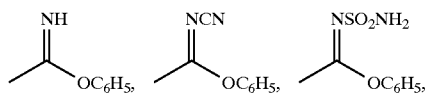

-continued

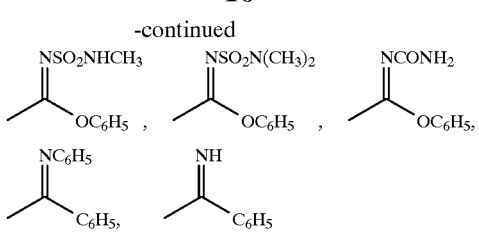

imidamido—represents a moiety of the formula

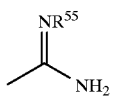

wherein and R⁵⁵ represents H, cyano, —SO₂NH₂, —SO₂NR⁴⁰R⁴², carboxamido, hydroxy and alkoxy. Representative imidamido groups can include, for example,

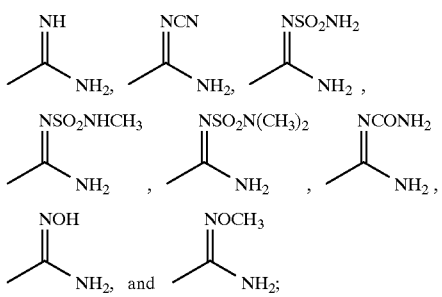

N-glycosyl—represents a pyranosyl or furanosyl monosaccharide. Representative N-glycosyl groups include (N→1)-tetra-O-acetyl-D-glucosyl, (N→1)-tetra-O-acetyl-D-galactosyl and (N→1)-tri-O-acetyl-D-ribosyl, e.g.

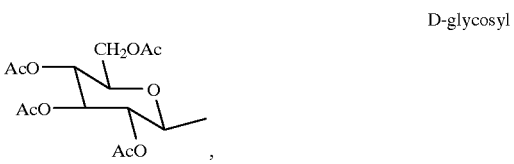
D-glycosyl

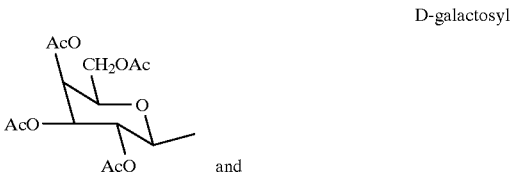
D-galactosyl

D-ribosyl 1-amino-2-nitroethenyl represents the formula:

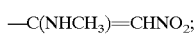

dialkylphosphinyl—represents a phosphine (—PO) moiety covalently bonded to two alkyl groups. A representative dialkylphosphinyl group is —PO(CH$_3$)$_2$.

sulfamoyl—represents a moiety of the formula —SO$_2$R$^{60}$ wherein R$^{60}$ represents amino, alkylamino and dialkylamino. Representative sulfamoyl groups can include, for example, —SO$_2$NH$_2$, —SO$_2$NHCH$_3$, —SO$_2$N(CH$_3$)$_2$.

sulfonyl—represents a moiety of the formula —SO$_2$R$^{60}$ wherein R$^{60}$ represents alkyl, aryl and arylalkyl. Representative sulfonyl groups can include, for example, —SO$_2$CH$_3$, —SO$_2$C$_6$H$_5$, —SO$_2$C$_6$H$_4$CH$_3$, and —SO$_2$CH$_2$C$_6$H$_5$.

Reference to the position of the substituents R$^1$, R$^2$, R$^3$, and R$^4$ is based on the numbered ring structure:

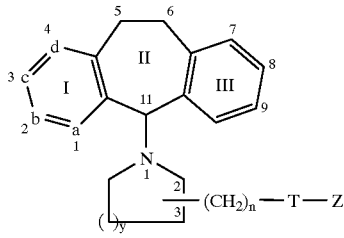

Certain compounds of the invention may exist in different stereoisomeric forms (e.g., enantiomers and diastereoisomers). The invention contemplates all such stereoisomers both in pure form and in mixture, including racemic mixtures. For example, the carbon atom at the C-11 position can be in the S or R stereoconfiguration. Also, the carbon atom at the C-2 and C-3 positions of the pyrrolidine (y=1) or at the C-2 position of the azetidine moiety (y=0) bonded at C-11 can also be in the S or R stereoconfiguration.

Certain tricyclic compounds will be acidic in nature e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention. Compounds of the present invention can be prepared according to the following Scheme 1:

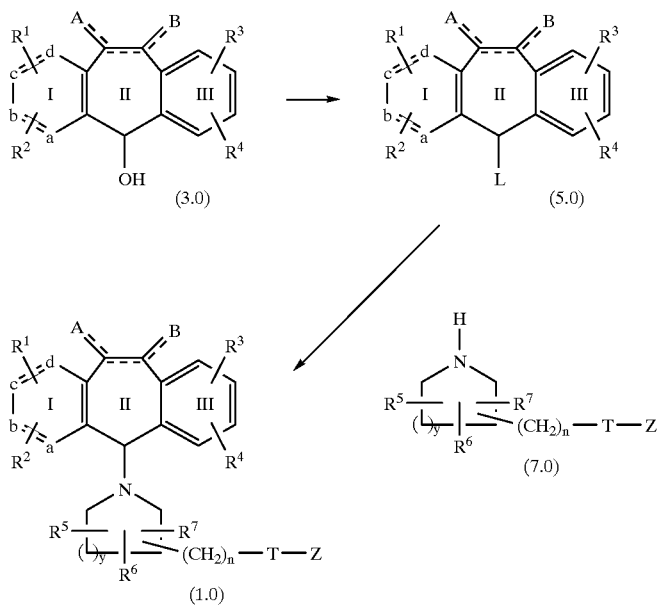

wherein L represents a leaving group such as halo, preferably chloro or a leaving group such as o-tosyl and o-mesyl; the dotted line represents a single or double bond; and a, b, c, d, A, B, R$^1$, R$^2$, R$^3$, R$^4$, R$^5$, R$^6$, R$^7$, m, n, T and Z are as defined hereinbefore.

Referring to the Scheme I, compounds of formula (5.0) can be prepared by reacting the compounds of formula (3.0)

with a halogenating agent or a sulfonylating agent in the presence of a suitable base, and optional aprotic solvent, in (i.e. an amide) can be prepared in accordance with Scheme 2.

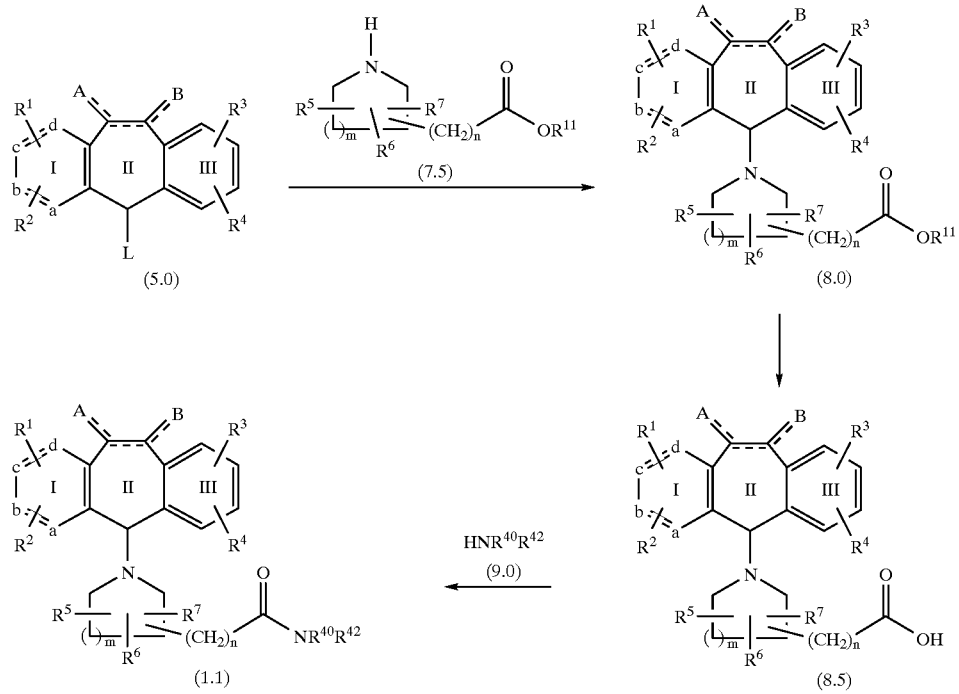

Scheme 2 amounts and under conditions effective to give compounds (5.0). Suitable bases include organic bases such as pyridine and triethylamine; or inorganic bases of alkali and alkaline earth metals including carbonates such as sodium, lithium, potassium and cesium carbonates, hydroxides such as sodium and potassium hydroxides; hydrides such as sodium or potassium hydride; and sodium t-butoxide, preferably sodium hydride. Suitable aprotic solvents include ethers, DMF, DMSO, THF, DME and mixtures thereof, preferably DMF. Preferably the halogenating agent is a chlorinating agent, such as thionyl chloride. The sulfonylating can be sulfonyl chloride, methane sulfonyl chloride or toluene sulfonyl chloride. The amounts of the halogenating agent or the sulfonylating agent can range from about one to about 10 moles per mole of compound (3.0). Temperatures can range from 0° to 50° C., or reflux of the reaction mixture.

The desired tricyclic piperidinyl compounds of formula (1.0) can be prepared by reacting the compounds of formula (5.0) with a suitably substituted pyrrolidine or azetidine compound of formula (7.0) in the presence of a suitable base and optional aprotic solvent, such as those described above, to give compounds (1.0). The amounts of the substituted pyrrolidine or azetidine compound of formula (7.0) to compound (5.0) can range from about one to about 10 moles per mole of compound (5.0) Temperatures can range from about room temperature to about 80° C.

The tricyclic compounds of formula (1.0) can be isolated from the reaction mixture using conventional procedures, such as, for example, extraction of the reaction mixture from water with organic solvents, evaporation of the organic solvents, followed by chromatography on silica gel or other suitable chromatographic media.

The compound of formula (1.0) wherein T=—CO— and Z=—NR$^{40}$R$^{42}$ wherein R$^{40}$ and R$^{42}$ are defined hereinbefore wherein L represents a leaving group, preferably chloro; the dotted line represents a single or double bond; and a, b, c, d, A, B, R$^1$, R$^2$, R$^3$, R$^4$, R$^5$, R$^6$, R$^7$, R$^{11}$, R$^{40}$, R$^{42}$, m and n are as defined hereinbefore.

Referring to the Scheme 2, compounds of formula (8.0) can be prepared by reacting the compounds of formula (5.0) with a piperdinyl carboxylic acid ester of formula (7.5) in the presence of a base and optional aprotic solvent, in amounts and under conditions effective to give compounds (8.0). Suitable bases and aprotic solvents are described hereinbefore. The amounts of compound (7.5) can range from about 1 to about 10 moles per mole of compound (5.0). Temperatures can range from room temperature to about 80° C. Compound (8.0) can be isolated as described hereinbefore.

Carboxylic acid compounds of formula (8.5) can be prepared by hydrolyzing carboxylic acid ester (8.0) with an excess amount of acid or base. Suitable acids include inorganic acids, organic acids or a mixture thereof. Inorganic acids include hydrogen chloride, hydrogen bromide, sulfuric acid, nitric acid, phosphoric acid, perchloric acid and the like. Organic acids include acetic, citric, formic, maleic, tartaric, methanesulfonic acid and arylsulfonic acids. Suitable bases, such as sodium hydroxide, or lithium hydroxide in an aqueous alcohol, have been described hereinbefore. The temperature can range from about 0° C. to about 100° C.

The desired amide compounds of formula (1.1) can be prepared by reacting the compounds of formula (8.5) with a suitable amine of formula (9.0) in the presence of a base and a suitable aprotic solvent effective to give amide compound (1.1). Suitable bases and aprotic solvents are described hereinbefore. The amounts of amine (9.0) can range from about 1 to about 10 moles per mole of carboxylic acid (8.5). Temperatures can range from 0° to 100° C. Compound (1.1) can be isolated as described hereinbefore.

Compounds of the present invention and preparative starting materials therof, are exemplified by the following examples, which should not be construed as limiting the scope of the disclosure.

EXAMPLE 1

Step A. 1-(3-Bromo-8-chloro-6,11-dihydro-5H-benzo[5,6]cyclohepta[1,2-b]pyridine-11-yl)-N-2-pyrrolidine methyl ester

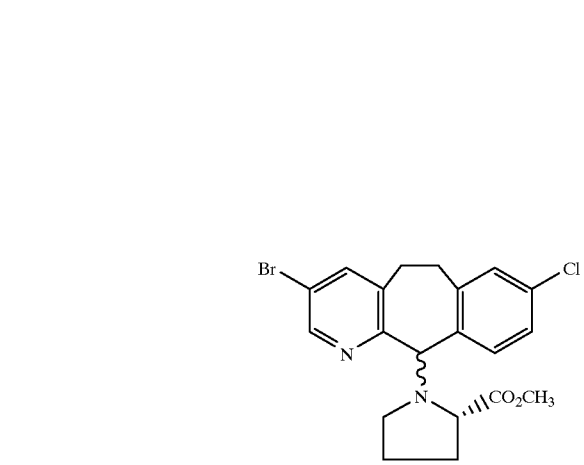

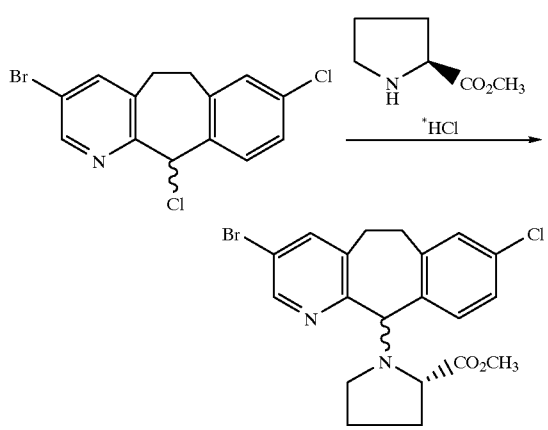

A mixture of 3-bromo-8,11-dichloro-6,11-dihydro-5H-benzo[5,6]cyclohepta[1,2-b]pyridine (1.05 g, 3.06 mmole), proline methyl ester hydrochloride (1.52 g 9.18 mmole) and N-methyl morpholine (1.85 g, 18.32 mmole) in DMF (15 mL) is heated at 85° C. overnight. The reaction mixture is evaporated to dryness, extracted with $CH_2Cl_2$ (100 mL), washed with water (2×100 mL), the organic extract is dried over $MgSO_4$ and the solvent evaporated to give an oily residue. The oily residue is flash chromatographed on a silica gel column eluting with hexane-15% ethyl acetate to give 0.78 g of the title compound, a foam. Partial PMR ($CDCl_3$, 200 MHz), 8.3 (s, 1H), 7.5 (d, 1H), 7–7.2 (m, 3H), 4.5 (s, 1H), 3.2 (s, 3H).

Step B. 1-(3-Bromo-8-chloro-6,11-dihydro-5H-benzo[5,6]cyclohepta[1,2-b]pyridine-11-yl)-N-(3-pyridinylmethyl)2-pyrrolidine carboxamide

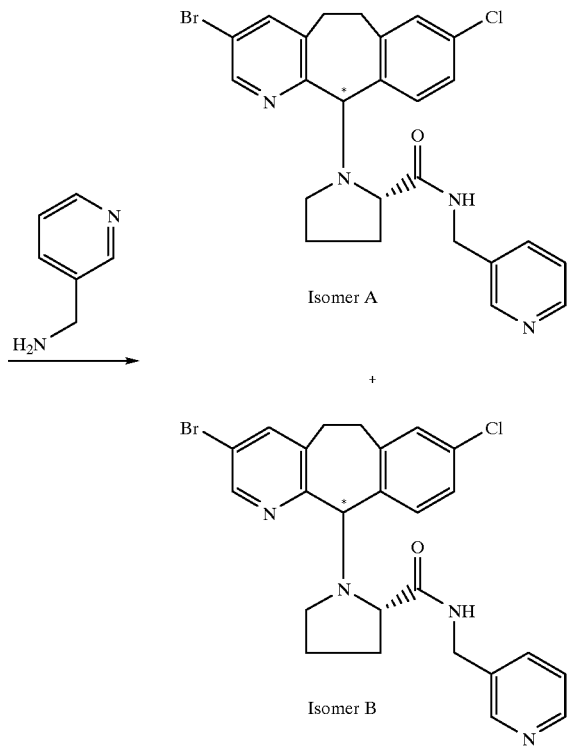

The title compound of Example 1, Step A (0.43 g, 9.1 mmole) and 3-aminomethylpyridine (0.196 g, 18.12 mmole) are heated at 130° C. overnight. The residue is chromatographed on a silica gel column eluting with $CH_2Cl_2$-3% ($CH_3OH$-10% conc $NH_4OH$), and separated to give the title compounds:

Isomer A, 0.062 g, Mass Spec. $MH^+513$ (FAB); partial PMR (CDCl3, 200 MHz), 8.45 (d, 1H), 8.4 (s, 1H), 8.3 (s, 1H), 7–7.4 (m, 6H), 4.68 (s, 1H) FPT $IC_{50}$=0.059 $\mu$M Isomer B, 0.042 g, Mass spec. $MH^+513$, partial PMR (CDCl3, 200 MHz), 8.55 (d, 1H), 8.4 (s, 1H), 8.35 (s, 1H), 6.8–7.6 (m, 6H). FPT $IC_{50}$=0.14 $\mu$M.

EXAMPLE 2

Step A. 1-(3,10-Dibromo-8-chloro-6,11-dihydro-5H-benzo[5,6]cyclohepta[1,2-b]pyridine-11-yl)-N-2-pyrrolidine methyl ester

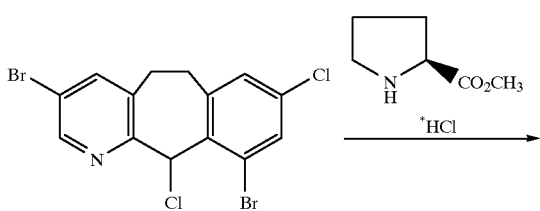

column eluting with hexane-15% ethyl acetate to give 0.43 g of the title compound as a foam. Partial PMR (CDCl₃, 200 MHz), 8.4 (d, 1H), 7.45 (d, 1H), 7.4 (d, 1H), 7.12 (d, 1H),5.56 (s, 1H), 5.01 (m, 1H), 3.55 (m, 1H), 3.23 (s, 3H).

Step B. 1-(3,10-dibromo-8-chloro-6,11-dihydro-5H-benzo[5,6]cyclohepta[1,2-b]pyridine-11-yl)-N-(3-pyridinylmethyl)-2-pyrrolidine carboxamide

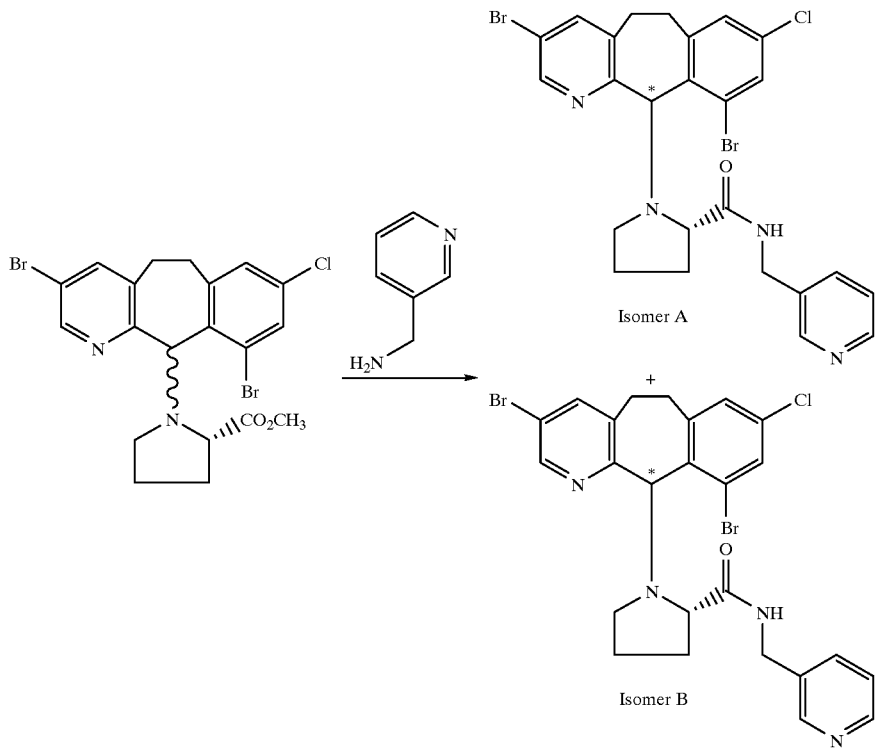

-continued

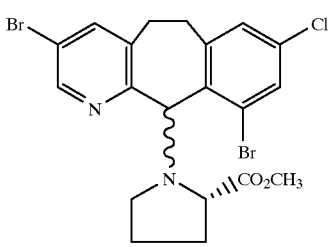

A mixture of 3,10-dibromo-8,11-dichloro-6,11-dihydro-5H-benzo[5,6]cyclohepta[1,2-b]pyridine (0.5 g, 1.18 mmole), proline methyl ester hydrochloride (0.59 g 3.55 mmole) and N-methyl morpholine (0.72 g, 7.11 mmole) in DMF (10 ML) is heated at 85° C. for one hour. The reaction mixture is evaporated to dryness, extracted with CH₂Cl₂ (100 mL) and washed with water (2×100 mL). The organic extract is dried over MgSO₄ and the solvent evaporated, leaving an oily residue which is flash chromatographed on a silica gel The compound of Example 2, Step A (0.36 g) is dissolved in ethanol (10 mL) and heated at 80° C. with 1N LiOH (aqueous, 4 mL) overnight. The pH is adjusted to 4 with 1N HCl and the solution evaporated to dryness. The product is dissolved in DMF (10 mL) and NMM (0.32 mL), and HOBT (0.187 g), DEC (0.265 g), and 3-amino methyl pyridine (0.16 mL) are added. The reaction mixture is stirred over the weekend, evaporated to dryness, the residue extracted in CH₂Cl₂ (100 mL) and with brine (2×100 mL). The organic extract is dried over MgSO₄, evaporated to dryness, and chromatographed on a Chiralpak® AD HPLC analytical chiral column (amylose tris(3,5-dimethylphenyl carbamate) coated on a 10 $\mu$M silica-gel substrate, trademark of of Chiral Technologies, Exton, Pa.)), using as the eluting solvent,eluting with 80% hexane/isopropanol (containing 0.25% diethylamine) to give the title compounds:

Isomer A (0.124 g) as a foam, Mass Spec. MH⁺591 (FAB); partial PMR (CDCl3, 400 MHz), 8.58 (d, 1H), 8.45 (s, 2H), 8.3 (s, 1H), 7.55 (s, 1H), 7.45(m, 2H),7.28 (m, 2H), 6.82 (s, 1H), 6.81 (t, 1H), 5.72 (s, 1H) FPT Inhibition: 15% @0.3 $\mu$M Isomer B, 0.165 g, Mass spec. MH⁺591, partial PMR (CDCl3, 400 MHz), 8.59 (d, 1H), 8.4 (m, 2H), 7.48 (s, 1H), 7.35 (m, 1H), 7.1–7.3 (m, 3H), 6.9 (t, 1H), 5.6 (s, 1H).
FPT IC₅₀=0.0052 $\mu$M

EXAMPLE 3

Step A. 1-(3-bromo-8-chloro-6,11-dihydro-5H-benzo[5,6]cyclohepta[1,2-b]pyridine-11-yl)-N-2-azetidine methyl ester

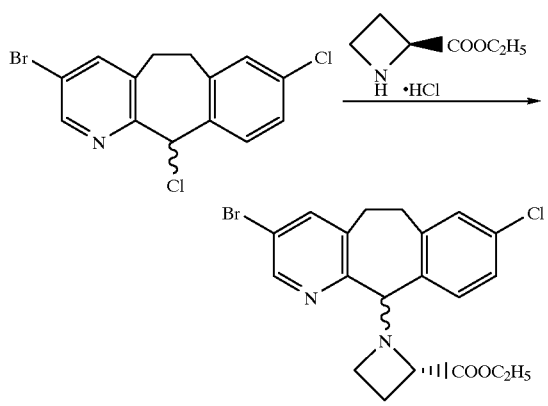

A mixture of 3-bromo-8,11-dichloro-6,11-dihydro-5H-benzo[5,6]cyclohepta[1,2-b]pyridine (1.05 g, 3.06 mmole), azetidine ethyl ester hydrochloride (1.52 g 6.02 mmole) and N-methyl morpholine (1.85 g, 18.32 mmole) in DMF (15 ML) is heated at 85° C. overnight. The reaction mixture is evaporated to dryness, extracted with $CH_2Cl_2$ (100 mL) and washed with water (2×100 mL). The organic extract is dried over $MgSO_4$ and the solvent is evaporated to give oily residue which is flash chromatographed on a silica gel column eluting with hexane-15% ethyl acetate, to give 0.72 g of the title compound as a foam. Partial PMR ($CDCl_3$, 200 MHz), 8.3 (s, 1H), 7.5 (d, 1H), 7–7.2 (m, 3H), 4.5 (s, 1H), 3.2 (s, 3H).

Step B. 1-(3-bromo-8-chloro-6,11-dihydro-5H-benzo[5,6]cyclohepta[1,2-b]pyridine-11-yl)-N-(3-pyridinylmethyl)2-azetidine carboxamide The compound of Example 3, Step A (0.7 g) is dissolved in ethanol (10 mL) and heated at 80° C. with 1N LiOH (aqueous, 3 mL) overnight. The pH is adjusted to 4 with 1N HCl and the solution evaporated to dryness. The product is dissolved in DMF (10 mL) and NMM (0.32 mL), and HOBT (0.187 g), DEC (0.265 g) and 3-aminomethyl pyridine (0.16 mL) are added. The reaction mixture is stirred over the week end at room temperature, evaporated to dryness, and the residue extracted in $CH_2Cl_2$ (100 mL). The organic extract is washed with brine (2×100 mL), dried over MgSO4, evaporated to dryness and the product is chromatographed on a Chiralpak® AD HPLC analytical chiral column eluting with 80% hexane/Isopropanol (containing 0.25% diethylamine) to give the title compounds:

Isomer A (0.113 g) as a foam, Mass Spec. $MH^+$499 (FAB); partial PMR (CDCl3, 400 MHz), 8.58 (d, 1H), 8.45 (s, 2H), 8.3 (s, 1H), 7.55 (s, 1H), 7.45(m, 2H),7.28 (m, 2H), 6.82 (s,1H), 6.81 (t, 1H), 5.72 (s, 1H) FPT $IC_{50}$=1.05 μM Isomer B (0.148 g) as a foam, Mass spec. $MH^+$499, partial PMR (CDCl3, 400 MHz), 8.59 (d, 1H), 8.4 (m, 2H), 7.48 (s, 1H), 7.35 (m, 1H), 7.1–7.3 (m, 3H), 6.9 (t, 1H), 5.6 (s, 1H) FPT Inhibition: 17% @0.1 μM

PREPARATION OF STARTING MATERIALS

Starting materials useful in preparing the compounds of the present invention are exemplified by the following preparative examples, which should not be construed to limit the scope of the disclosure. The tricylic compounds (3.0) and substituted piperidinyl compounds (7.0) used as starting materials are known in the art and/or can be prepared using known methods, such as taught in U.S. Pat. Nos. 5,089,496; 5,151,423; 4,454,143; 4,355,036; PCT/US94/11390 (WO95/10514); PCT/US94/11391 (WO 95/10515); PCT/US94/11392 (WO95/10516); Stanley R. Sandler and Wolf Karo, Organic Functional Group Preparations, 2nd Edition, Academic Press, Inc., San Diego, Calif., Vol. 1–3, (1983); in J. March, Advanced Organic Chemistry, Reactions & Mechanisms, and Structure, 3rd Edition, John Wiley

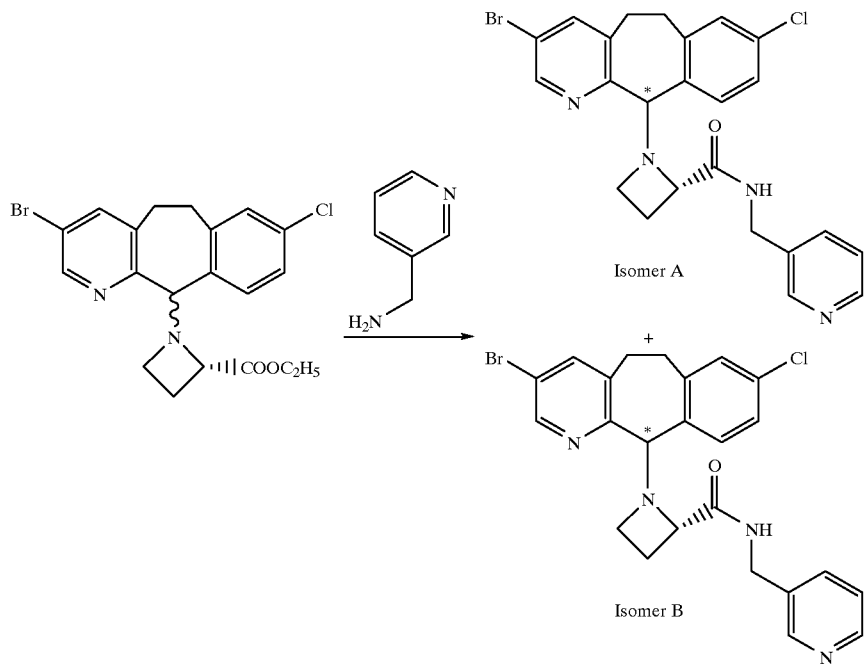

& Sons, New York, 1346 pp. (1985); A. J. Boulton and A. McKillop (Eds.), Comprehensive Heterocyclic Chemistry, Volume 7, Four Membered Rings With One Nitrogen Atom, Pergamon Press, Elmsford, N.Y., (1960–1985); A. J. Boulton and A. McKillop (Eds.), Comprehensive Heterocyclic Chemistry, Volume 4, Part 3, Five Membered Rings With One Nitrogen Atom, Pergamon Press, Elmsford, N.Y., (1960–1985); J. Am. Chem. Soc. 80, pg. 970 (1958); JOC 33, 3637 (1968); Tetra. Letters, pp. 381–382 (1995); Helvetics. Chem. Acta, 59 (6), pp. 1917–24 (1976); and J. Med. Chem., 33, 71–77 (1990). The starting materials may also be prepared as taught in U.S. application Ser. No. 08/410,187 filed Mar. 24, 1995, U.S. Pat. No. 5,719,148 U.S. application Ser. No. 08/577,951 filed Dec. 22, 1995, and abandoned U.S. application Ser. No. 08/615,760 filed Mar. 13, 1996 abandoned; the disclosures being incorporated herein by reference. Alternative mechanistic pathways and analogous structures within the scope of the invention may be apparent to those skilled in the art.

For example, the pyrrolidine compounds of formula (7.0), wherein T=—CO— can be prepared by initially preparing a pyrole compound substituted with the requisite 2- or 3-$(CH_2)_n COZ$ moiety, together any optional -$R^5$, -$R^6$, -$R^7$ and/or -$R^8$ moieties, as described in the references cited above and/other known art. The 2- or 3-substituted pyrole compound can subsequently be reduced using conventional reduction procedures, such as catalytic hydrogenation, to give the desired pyrrolidine compound (7.0). One skilled in the art will appreciate that in cases where -$R^5$, -$R^6$, -$R^7$, -$R^8$ and/or Z moieties also contain reducible groups, it may useful to utilize alternative methods.

The azetidine compounds of formula (7.0) wherein T is —CO— can be prepared by reacting the azetidine 2- or -3-carboxylic acid chloride with

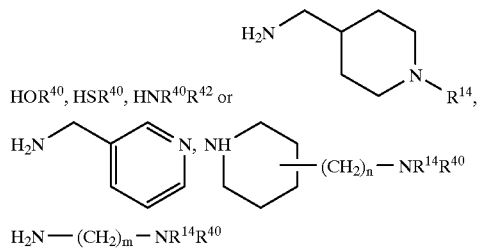

in a solvent such as methylene chloride in the presence of a base such as triethylamine.

Also, the azetidine compounds of formula (7.0) wherein Z is alkyl, aryl, aralkyl, heteroalkyl, heteroaryl, heteroarylalkyl, heterocycloalkyl, heterocycloalkylalkyl, —$CR^{40}R^{42}$ can be prepared by reacting the azetidine 2- or -3-carboxylic acid chloride with a Grignard reagent of the formula MgBr of the above alkyl groups, i.e. MgBralkyl and MgBr$CR^{40}R^{42}$, in a solvent such as THF.

The azetidine or pyrrolidine compounds of formula (7.0), wherein T=—$CR^{30}R^{31}$- can be prepared by reacting an N—BOC-azetidine or pyrrolidine 2- or 3-one compound with MgBr$CR^{30}R^{31}$Z to give a tertiary hydroxy compound. The hydroxy group on the tertiary hydroxy compound is removed using reducing reagent such as tributyltinhydride via free radical mechamism (through xanthate intermediate) to give a product which is subsequently treated with TFA to give the desired azetidine or pyrrolidine compound (7.0).

The sulfonylazetidine or pyrrolidine compounds of formula (7.0), wherein T=—$SO_2$- can be prepared by reacting the appropriate 2- or 3-hydroxy-N-blocked-azetidine or pyrrolidine (prepared by reducing, for example, with sodium borohydride, an N-blocked 2- or 3-azetidine or pyrolidine 2- or 3-one) with a suitable chlorinating agent such as thionyl chloride to obtain the 2- or 3-chloro-N-blocked azetidine or pyrrolidine, using N-blocking groups such as benzyloxycarbonyl or tert-butoxycarbonyl. The 2- or 3-chloro-N-blocked azetidine or pyrrolidine can then be reacted with sodium bisulfite to obtain the corresponding 2- or 3-sulfonic acid N-blocked azetidine or pyrrolidine sodium salt. This salt is then reacted with an appropriate chlorinating agent such as phosphorus pentachloride or phosphorus oxychloride to obtain the corresponding 2- or 3-sulfonylchloride-N-blocked azetidine or pyrrolidine. This sulfonyl chloride compound is then reacted with a corresponding agent containing the desired Z group (i.e. amines, alkylating agents and the like) to obtain the desired sulfonylazetidine or pyrrolidine (7.0).

The sulfoxylazetidine or pyrrolidine wherein T=—SO— (with the proviso that Z is not -$NR^{40}R^{42}$) can be prepared by reacting the appropriate 2- or 3-hydroxy-N-blocked-azetidine or pyrrolidine with a suitable chlorinating agent such as thionyl chloride to obtain the 2- or 3-chloro-N-blocked azetidine or pyrrolidine, using N-blocking groups such as benzyloxycarbonyl or tert-butoxycarbonyl. The 2- or 3-chloro-N-blocked azetidine or pyrrolidine can then reacted with the corresponding substituted sulfide (i.e. arylsulfide, alkylsulfides and the like) to obtain the appropriate 2- or 3-sulfide-N-blocked azetidine or pyrrolidine. This compound can then be reacted with an oxidizing agent such as metachloroperbenzoic acid to obtain the desired sulfoxylazetidine or pyrrolidine (7.0).

PREPARATIVE EXAMPLE

Step A

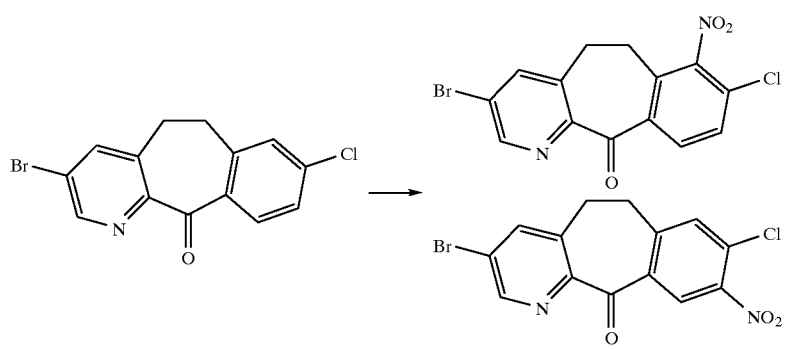

Combine 40.0 g (0.124 mole) of the starting ketone and 200 mL of $H_2SO_4$ and cool to 0° C. Slowly add 13.78 g (0.136 mole) of $KNO_3$ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B

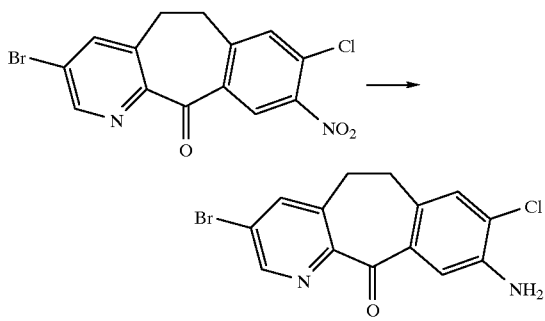

React 28 g (76.2 mmol) of the 9-nitro product of Step A, 400 mL of 85% EtOH/water, 3.8 g (34.3 mmol) of CaCl$_2$ and 38.28 g (0.685 mole) of Fe using substantially the same procedure as described for Preparative Example 4, Step C, to give 24 g of the product Step C

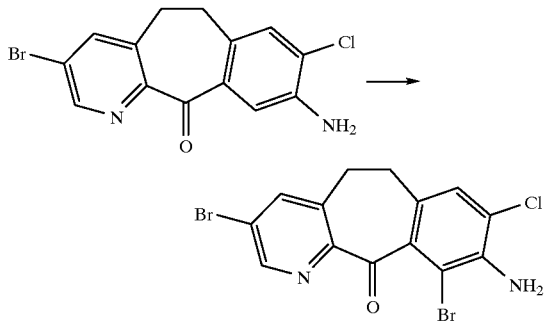

Combine 13 g (38.5 mmol) of the product of Step B, 140 mL of HOAc and slowly add a solution of 2.95 mL (57.8 mmol) of Br$_2$ in 10 mL of HOAc over a period of 20 min. Stir the reaction mixture at room temperature, then concentrate in vacuo to a residue. Add CH$_2$Cl$_2$ and water, then adjust to pH=8–9 with 50% NaOH (aqueous). Wash the organic phase with water, then brine and dry over Na$_2$SO$_4$. Concentrate in vacuo to give 11.3 g of the product.

Step D

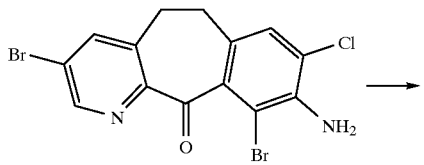

-continued

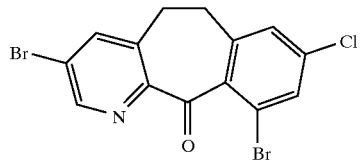

Cool 100 mL of concentrated HCl (aqueous) to 0° C., then add 5.61 g (81.4 mmol) of NaNO$_2$ and stir for 10 min. Slowly add (in portions) 11.3 g (27.1 mmol) of the product of Step C and stir the mixture at 0°–3° C. for 2.25 hrs. Slowly add (dropwise) 180 mL of 50% H$_3$PO$_2$ (aqueous) and allow the mixture to stand at 0° C. overnight. Slowly add (dropwise) 150 mL of 50% NaOH over 30 min., to adjust to pH=9, then extract with CH$_2$Cl$_2$. Wash the extract with water, then brine and dry over Na$_2$SO$_4$. Concentrate in vacuo to a residue and chromatograph (silica gel, 2% EtOAc/CH$_2$Cl$_2$) to give 8.6 g of the product.

Step E

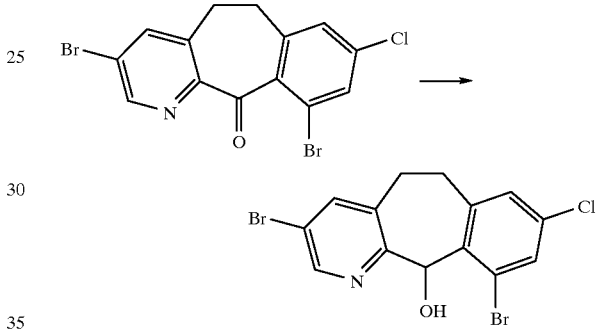

Combine 8.6 g (21.4 mmol) of the product of Step D and 300 mL of MeOH and cool to 0°–2° C. Add 1.21 g (32.1 mmol) of NaBH$_4$ and stir the mixture at ~0° C. for 1 hr. Add another 0.121 g (3.21 mmol) of NaBH$_4$, stir for 2 hr. at 0° C., then let stand overnight at 0° C. Concentrate in vacuo to a residue then partition the residue between CH$_2$Cl$_2$ and water. Separate the organic phase and concentrate in vacuo (50° C.) to give 8.2 g of the product.

Step F. 3,10-dibromo-8,11-dichloro-6,11-dihydro-5H-benzo[5,6]cyclohepta[1,2-b]pyridine

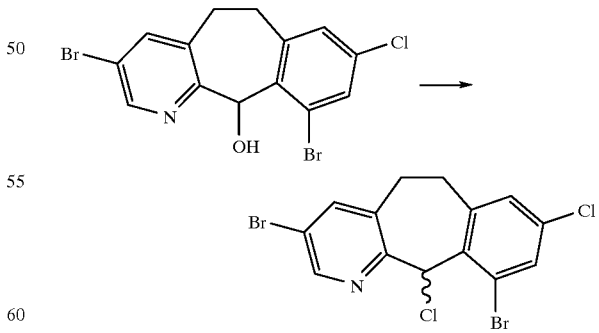

Combine 8.2 g (20.3 mmol) of the product of Step E and 160 mL of CH$_2$Cl$_2$, cool to 0° C., then slowly add (dropwise) 14.8 mL (203 mmol) of SOCl$_2$ over a 30 min. period. Warm the mixture to room temperature and stir for 4.5 hrs., then concentrate in vacuo to to give the title compound.

ASSAYS

1. In vitro enzyme assays: FPT $IC_{50}$ (inhibition of farnesyl protein transferase, in vitro enzyme assay) are determined by the methods disclosed in WO/10515 or WO 95/10516. The data demonstrate that the compounds of the invention are inhibitors of Ras-CVLS farnesylation by partially purified rat brain farnesyl protein transferase (FPT). The data also show that there are compounds of the invention which can be considered as potent ($IC_{50}$<10 $\mu$M) inhibitors of Ras-CVLS farnesylation by partially purified rat brain FPT.

2. Cell-based assay. COS $IC_{50}$ values refer to the COS cells activity inhibition of Ras processing, are determined by the methods disclosed in WO/10515 or WO 95/10516.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

Example A—Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B—Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

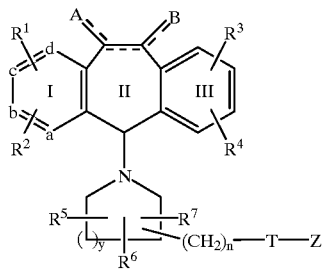

(1.0)

or a pharmaceutically acceptable salt or solvate thereof, wherein:

one of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or each $R^1$ and each $R^2$ is independently selected from H, halo, $-CF_3$, $-OR^{10}$, $-COR^{10}$, $-SR^{10}$, $-S(O)_tR^{11}$ (wherein t is 0, 1 or 2), $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR^{10}$, $-CONHCH_2CH_2OH$, $-NR^{10}COOR^{11}$, $-SR^{11}C(O)OR^{11}$, $-SR^{11}N(R^{75})_2$ wherein each $R^{75}$ is independently selected from H and $-C(O)OR^{11}$, benzotriazol-1-yloxy, tetrazol-5-ylthio, or substituted tetrazol-5-ylthio, alkynyl, alkenyl or alkyl, said alkyl or alkenyl group optionally being substituted with halo, $-OR^{10}$ or $-CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$ and $R^6$ (y=0) or $R^5$, $R^6$ and $R^7$ (y=1) each independently represents H, $-CF_3$, $-COR^{10}$, alkyl or aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R^{11}$, $-CO_2R^{10}$, $OPO_3R^{10}$ or $R^5$ is combined with $R^6$ or $R^7$ to represent $=O$ or $=S$;

$R^{10}$ independently represents H, alkyl, cycloalkyl, cycloalkylalkyl, heteroaryl, aryl, aralkyl or $-NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl, cycloalkylalkyl, alkenyl and alkynyl;

$R^{11}$ represents alkyl or aryl;

the dotted line between carbon atoms 5 and 6 represents an optional double bond, such that when a double bond is present, A and B independently represent $-NO_2$, $-R^{10}$, halo, $-OR^{11}$, $-OCO_2R^{11}$ or $-OC(O)R^{10}$, and when no double bond is present between carbon atoms 5 and 6, A and B each independently represent $H_2$, $-(OR^{11})_2$, H and halo, dihalo, alkyl and H, (alkyl)$_2$, $-H$ and $-OC(O)R^{10}$, H and $-OR^{10}$, oxy, aryl and H, $=NOR^{10}$ or $-O-(CH_2)_p-O-$ wherein p is 2, 3 or 4; and y is 0 (zero) or 1;

n is 0, 1, 2, 3, 4, 5 or 6;

T is $-CO-$; $-SO-$; $-SO_2-$; or $-CR^{30}R^{31}-$ wherein $R^{30}$ and $R^{31}$ independently represent H, alkyl, aryl, aralkyl, heteroalkyl, heteroaryl, heteroarylalkyl, heterocycloalkyl or heterocycloalkylalkyl; and Z represents alkyl, aryl, aralkyl, heteroalkyl, heteroaryl, heteroarylalkyl, heterocycloalkyl, heterocycloalkylalkyl, $-OR^{40}$, $-SR^{40}$, $-CR^{40}R^{42}$, $-NR^{40}R^{42}$,

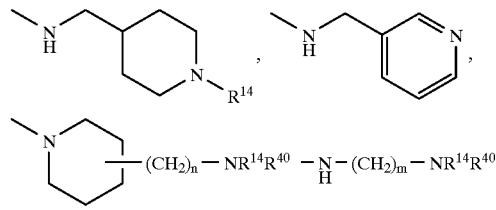

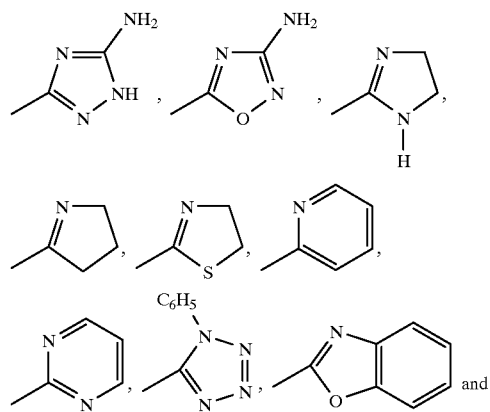

wherein n, $R^{40}$ and $R^{42}$ are defined hereinbefore, m is 2, 3 4, 5, 6, 7 or 8;

and $R^{14}$ represents H, $C_{1-6}$ alkyl, aralkyl, acyl, carboxamido, cyano, alkoxycarbonyl, aralkyloxycarbonyl, D-amino acids covalently bonded through the carboxyl group, imido, imidamido, sulfamoyl, sulfonyl, dialkylphosphinyl, N-glycosyl, $-C(NHCH_3)=CHNO_2$, with the proviso that when T is $-SO-$, Z is not $-NR^{40}R^{42}$.

2. The compound of claim 1 wherein a is N; b, c and d are carbon; A and B each represent $H_2$ and the optional double bond is absent.

3. The compound of claim 2 wherein $R^1$ and $R^4$ are H and $R^2$ and $R^3$ are halo selected from chloro and bromo; or $R^1$ is H and $R^2$, $R^3$ and $R^4$ are halo selected from chloro and bromo.

4. The compound of claim 2 wherein $R^2$ is halo in the 3-position and $R^3$ is halo in the 8-position.

5. The compound of claim 2 wherein $R^2$ is Br in the 3-position and $R^3$ is Cl in the 8-position.

6. The compound of claim 2 wherein $R^1$ is H and $R^2$, $R^3$ and $R^4$ are halo selected from chloro and bromo.

7. The compound of claim 2 wherein $R^2$ is halo in the 3-position, $R^3$ is halo in the 8-position and $R^4$ is halo in the 10-position.

8. The compound of claim 2 wherein $R^2$ is bromo in the 3-position, $R^3$ is chloro in the 8-position and $R^4$ is bromo in the 10-position.

9. The compound of claim 3 wherein the moiety $-(CH_2)_n-T-Z$ is bonded at the 2-position on the pyrrolidine (y=1) or azetidine (y=0) ring.

10. The compound of claim 9 wherein n is zero; T is —CO— and Z is —NR$^{40}$R$^{42}$.

11. The compound of claim 10 wherein R$^{40}$ is H; and R$^{42}$ is 3-pyridylmethyl.

12. The compound of claim 1 selected from the group consisting of:

1-(3-Bromo-8-chloro-6,11-dihydro-5H-benzo[5,6] cyclohepta[1,2-b]pyridine-11-yl)-N-(3-pyridinylmethyl) 2-pyrrolidine carboxamide;
1-(3,10-dibromo-8-chloro-6,11-dihydro-5H-benzo[5,6] cyclohepta[1,2-b]pyridine-11-yl)-N-(3-pyridinylmethyl)-2-pyrrolidine carboxamide; and
1-(3-bromo-8-chloro-6,11-dihydro-5H-benzo[5,6] cyclohepta[1,2-b]pyridine-11-yl)-N-(3-pyridinylmethyl) 2-azetidine carboxamide.

13. The compound of claim 1 which is selected from

Isomer A
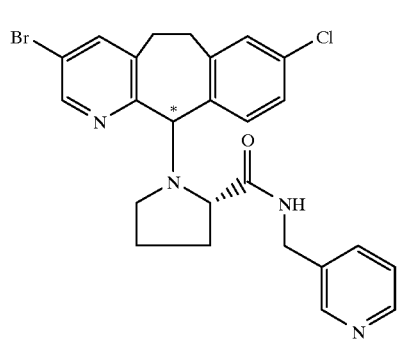

Isomer B
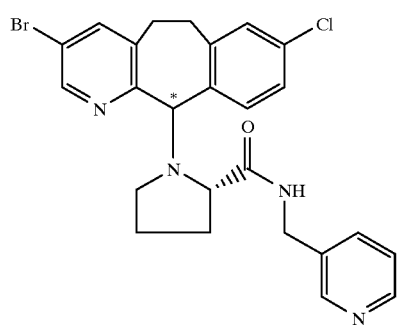

Isomer A
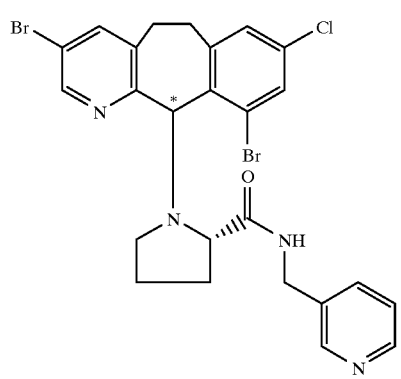

Isomer B
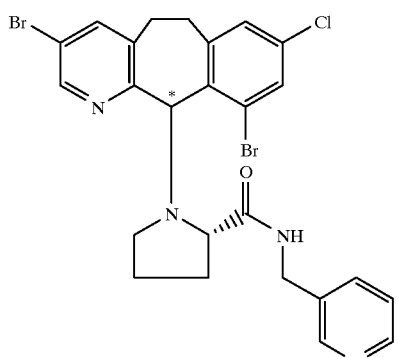

Isomer A
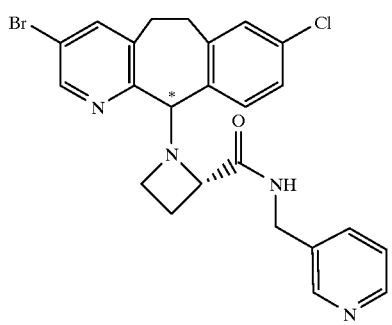

Isomer B
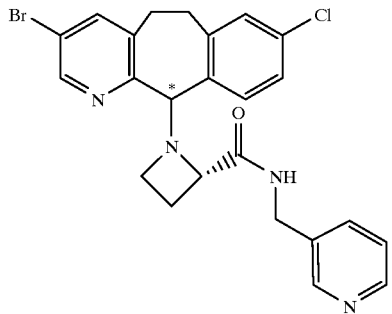

or a pharmaceutically acceptable salt thereof.

14. The compound of claim 13 which is

Isomer B
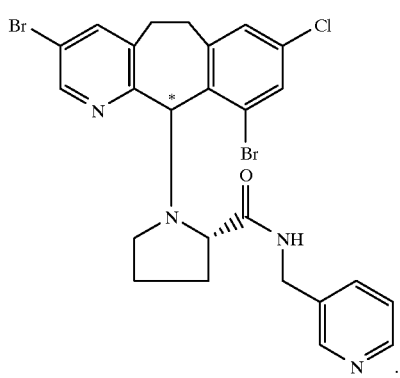

15. A pharmaceutical composition comprising an effective amount of compound of claim 1 in combination with a pharmaceutically acceptable carrier.

16. A method for inhibiting the abnormal growth of tumor cells expressing an activated ras oncogene by inhibition of ras farnesyl protein transferase in a mammal comprising administering to a mammal in need thereof an effective amount of a compound of claim 1.

17. The method of claim 16 wherein the cells inhibited are pancreatic tumor cells, lung tumor cells, myeloid leukemia tumor cells, thyroid follicular tumor cells, myelodysplastic tumor cells, epidermal carcinoma tumor cells, bladder tumor cells or colon tumor cells.

* * * * *